United States Patent [19]

Stähler et al.

[11] 4,447,444

[45] May 8, 1984

[54] 1-ALKYL-3-ALKOXYMETHYL-4-ALKOXY-5-DIALKYLCARBAMOYLOXY PYRAZOLES AND USE AS APHICIDES

[75] Inventors: Gerhard Stähler; Anna Waltersdorfer, both of Frankfurt am Main, Fed. Rep. of Germany

[73] Assignee: Hoechst Aktiengesellschaft, Frankfurt am Main, Fed. Rep. of Germany

[21] Appl. No.: 457,699

[22] Filed: Jan. 13, 1983

Related U.S. Application Data

[63] Continuation-in-part of Ser. No. 227,236, Jan. 22, 1981, abandoned.

[30] Foreign Application Priority Data

Jan. 24, 1980 [DE] Fed. Rep. of Germany ....... 3002413

[51] Int. Cl.³ .................... A01N 43/56; C07D 231/28
[52] U.S. Cl. ................................ 424/273 P; 548/376; 548/377
[58] Field of Search .............................. 548/376, 377; 424/273 P

[56] References Cited

U.S. PATENT DOCUMENTS 4,126,690  11/1978  Maurer et al. ..................... 548/377

FOREIGN PATENT DOCUMENTS 2603215  8/1977  Fed. Rep. of Germany ...... 548/116

OTHER PUBLICATIONS

Kay et al., J. Chem. Soc. (C) 1970, pp. 445–448.

Primary Examiner—Henry R. Jiles
Assistant Examiner—Kurt G. Briscoe
Attorney, Agent, or Firm—Curtis, Morris & Safford

[57] ABSTRACT

Compounds of the formula I

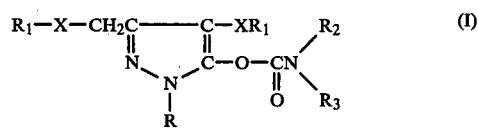

in which R is hydrogen, (subst.) alkyl, cycloalkyl, benzyl, phenylethyl or (subst.) phenyl, $R_1$, $R_2$ and $R_3$ are alkyl and X is oxygen or sulfur are effective insecticides and acaricides and especially suitable for combating plant lice.

6 Claims, No Drawings

1-ALKYL-3-ALKOXYMETHYL-4-ALKOXY-5-DIALKYLCARBAMOYLOXY PYRAZOLES AND USE AS APHICIDES

This is a continuation-in-part application of our co-pending application Ser. No. 227,236 filed Jan. 22, 1981 by Stähler et al., abandoned.

This invention relates to novel N,N-dialkyl-O-[pyrazol-5-yl]-carbamic acid esters of the formula I $$R_1-X-CH_2C\underset{\underset{\underset{R}{N}}{N}}{\overset{\overset{}{\|}}{C}}\underset{}{\overset{\overset{}{\|}}{C}}-XR_1 \quad R_2 \atop C-O-C\underset{\underset{R_3}{\|}}{N} \quad \text{(I)}$$

in which

R is hydrogen, $C_1$-$C_8$alkyl optionally substituted with CN, $C_1$-$C_4$alkoxy or $C_1$-$C_4$alkylmercapto, or is $C_5$-$C_6$-cycloalkyl, benzyl, phenylethyl or phenyl optionally substituted with 1-3 chlorine, bromine, $C_1$-$C_3$alkyl or $C_1$-$C_3$alkoxy, $R_1$, $R_2$ and $R_3$ are $C_1$-$C_4$alkyl and X is oxygen or sulfur.

The compounds of the invention can be prepared by reacting pyrazolones of the formula II $$R_1-X-CH_2-\underset{\underset{\underset{R}{N}}{N}}{\overset{\overset{}{\|}}{C}}\underset{}{\overset{\overset{}{}}{-}}CHXR_1 \atop C=O \quad \text{(II)}$$

in which R and $R_1$ are as defined under formula I, in the presence of acid acceptors or in the form of their alkali metal, alkaline earth metal or ammonium salts, with N,N-dialkylcarbamic acid halides of the formula III $$\underset{R_3}{\overset{R_2}{\diagdown}}\text{NCHal} \atop \overset{\|}{O} \quad \text{(III)}$$

The N,N-dialkylcarbamic acid chlorides used as starting compounds III are known and can be presented by known methods. The pyrazolones of the formula II can be obtained by reacting substituted hydrazines of the formula IV $$\text{RNHNH}_2 \quad \text{(IV)}$$

with acetoacetic acid ester derivatives of the formula V $$R_1XCH_2C\underset{\overset{\|}{O}}{}-\overset{XR_1}{\underset{}{CH}}-COOAlkyl(C_1\text{-}C_4) \quad \text{(V)}$$

The compounds of the formula V can be prepared as described in literature by Claisen acetoacetic acid ester condensation of 2 mols of alkoxy- or alkylmercapto-acetoacetic acid ester.

The reaction to obtain the compounds of the invention is preferably carried out in inert solvents or diluents, such as, for example, aliphatic and aromatic, optionally chlorinated, hydrocarbons, for example benzene, toluene xylene, chlorobenzene, methylene chloride, chloroform, carbon tetrachloride, 1,2-dichloroethane, or ethers such as diethyl, dipropyl, dibutyl, or glycoldimethyl ether; ketones for example acetone or methylethylketone, or nitriles such as acetonitrile or propionitrile.

The pyrazolones II can be reacted with the N,N-dialkylcarbamic acid chlorides in the form of the alkali metal salts of their tautomeric enol forms or as such in the presence of an acid acceptor. Suitable acceptors are e.g. alkali metal carbonates or alcoholates such as sodium carbonate, potassium carbonate or potassium tert-.butylate, or organic bases, for example triethylamine, dimethylaniline and pyridine.

The reaction generally is carried out at atmospheric pressure and at temperatures between room temperature and 100° C., preferably between 30° and 70° C.

The starting compounds are usually reacted in stoichiometric amounts or the N,N-dialkylcarbamic acid chloride is used in a slight excess.

The reaction products are sometimes obtained as solids of low melting points but more frequently as undistillable oils. They are characterized by an outstanding selective insecticidal and acaricidal efficiency, in particular against aphids (plant lice). Their systemic effect is particularly noteworthy. This is to say that they exhibit their effect after having been absorbed by the green parts as well as the root system of the plants. It is therefore possible to use them for combating plant lice species living in hidden places inside of plant galls and other parts of the plants that are difficult to reach.

Plant lice species that can be effectively combated with the compounds of the invention include the green peach aphid (*Myzus persicae*), the black bean aphid (*Aphis fabae*), the bird cherry aphid (*Rhopalosiphum padi*), the green pea louse (*Acyrtosiphon pisum*), the mealy cabbage aphid (*Brevicoryne brassicae*), the red currant aphid (*Crytomyzus ribis*), the mealy apple louse (*Dysaphis radicicola*), the black cherry aphid (*Myzus cerasi*) and the woolly apple aphid (*Eriosoma lanigerum*).

The compounds of the invention can also be used for combating a number of other insect pests, for example those belonging to the classes of Orthoptera, Heteroptera, Homoptera, Lepidoptera, Hymenoptera, Diptera, Coleoptera and Acarina occurring in agriculture, forestry, in stockpiling and in the field of sanitation.

The selectivity of the compounds of the invention becomes manifest furthermore by their low toxicity in animal organisms which are useful for man, especially beneficial insects such as the honey-bee, or organisms being an important member in the ecological chain, for example the water-flea (*Daphnia magna*). Beneficial animal organisms are furthermore those which are enemies of the insects or acaridae to be combated and thus participate in diminishing the populations thereof. In the case of aphids (plant lice), for example, these enemies are the insects of prey Syrphus sp., Chrysopa sp., Coccinella sp., or the parasites Trichogramma sp. These organisms, too, are damaged to a lower degree by the compounds of Formula I than the aphids to be combated.

It is, therefore, another object of the present invention to provide pesticidal compositions containing as active ingredient an effective amount of compounds of the formula I.

The compositions of the invention generally contain 2 to 80% by weight of active ingredients. They can be applied in the form of wettable powders, emulsifiable concentrates, sprayable solutions, dusting agents, or granules formulated in conventional manner.

Wettable powders are formulations which are uniformly dispersible in water and which, in addition to the active compound and a diluent or inert material, also contain wetting agents, for example, polyoxethylated alkylphenols, polyoxethylated fatty alcohols, alkylsulfonates or alkylphenylsulfonates and dispersing agents, for example sodium ligninsulfonate, sodium-2,2'-dinaphthylmethane-6,6'-disulfonate, sodium dibutylnaphthalene sulfonate or the sodium salt of oleoylmethyl taurine.

Emulsifiable concentrates are obtained by dissolving the active compound in an organic solvent, for example, butanol, cyclohexanone, dimethyl formamide, xylene or higher-boiling aromatic or aliphatic hydrocarbons with addition of one or several emulsifiers. Suitable emulsifiers are, for example, calcium salts of alkylarylsulfonic acids such as calcium dodecylbenzenesulfonate, or non-ionic emulsifiers such as fatty acid polyglycol esters, alkylarylpolyglycol ethers, fatty alcohol polyglycol ethers, propylene oxide ethylene oxide condensation products, fatty alcohol/propylene oxide/ethylene oxide condensation products, alkyl polyethers, sorbitan fatty acid esters, polyoxyethylenesorbitan-fatty acid esters, or polyoxyethylene sorbit esters.

Dusting agents are obtained by grinding the active compound with finely divided solids, for example talc, natural clays, such as kaolin, bentonite, pyrophilite or diatomaceous earth.

Granules can be manufactured either by spraying the active compound onto absorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules, if desired in admixture with fertilizers.

In wettable powders, the active compound concentration varies, for example, between about 10 and 80%, the remainder consisting of one or more of the above-mentioned formulation additives. In the case of emulsifiable concentrates, the active compound concentration is about 10 to 80%. Dust formulations usually contain 5-20% of active compound, and sprayable solutions about 2-20%. In the case of granules, the active compound content in part depends on whether the active compound is in a liquid or solid form and what granulating auxiliaries, fillers and the like are used.

The active compounds according to the invention can be combined with fungicides or with other insecticides and acaricides.

The following examples illustrate the invention.

(A) EXAMPLES OF PREPARATION

Example 1

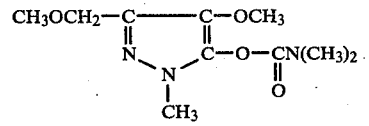

17 g of 1-methyl-3-methoxymethyl-4-methoxypyrazolone-5 are dissolved in 150 ml of absolute acetonitrile. After addition of 12 g potassium tert.butylate, the reaction mixture is stirred until it is homogeneous, 11 g of dimethylcarbamic acid chloride are added and the whole is heated for 2 hours to 50°–60° C. The solvent is then distilled off at 100 to 200 Torr in a rotary evaporator. The residue is taken up in 150 ml of methylene chloride and extracted twice with 30 ml of water each. The methylene chloride phase is separated, dried with anhydrous sodium sulfate and concentrated by evaporation in a slight vacuum. 23 g of 1-methyl-3-methoxymethyl-4-methoxy-5-dimethylcarbamoyloxypyrazole (94.7% of the theoretical) are obtained as a light brown oil, $n_D^{23} = 1.4970$.

The compounds of the general formula

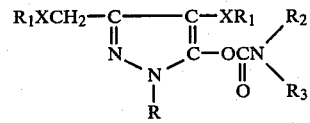

listed in the following table were prepared in analogous manner.

| Example No. | R | $R_1$ | $R_2$ | $R_3$ | X | Physical Data |
|---|---|---|---|---|---|---|
| 2 | —CH$_4$ | —CH$_3$ | —CH$_3$ | —CH$_3$ | S | Fp. 87–89° C. |
| 3 | —CH$_3$ | —C$_2$H$_5$ | —CH$_3$ | —CH$_3$ | O | $n_D^{23}$ = 1.4849 |
| 4 | —CH$_3$ | —C$_2$H$_5$ | —CH$_3$ | —CH$_3$ | S | $n_D^{23}$ = 1.5360 |
| 5 | —C$_2$H$_5$ | —CH$_3$ | —CH$_3$ | —CH$_3$ | O | $n_D^{23}$ = 1.4922 |
| 6 | —C$_2$H$_5$ | —CH$_3$ | —CH$_3$ | —CH$_3$ | S | Fp. 56–58° C. |
| 7 | —C$_2$H$_5$ | —C$_2$H$_5$ | —CH$_3$ | —CH$_3$ | S | $n_D^{23}$ = 1.5217 |
| 8 | —CH$_2$CH$_2$CN | —CH$_3$ | —CH$_3$ | —CH$_3$ | O | $n_D^{23}$ = 1.4997 |
| 9 | —CH$_2$CH$_2$CN | —CH$_3$ | —CH$_3$ | —CH$_3$ | S | $n_D^{23}$ = 1.5270 |
| 10 | —C$_3$H$_{7(n)}$ | —CH$_3$ | —CH$_3$ | —CH$_3$ | O | $n_D^{23}$ = 1.4831 |
| 11 | —C$_3$H$_{7(n)}$ | —CH$_3$ | —CH$_3$ | —CH$_3$ | S | Fp. 55–56° C. |
| 12 | —C$_3$H$_{7(n)}$ | —C$_2$H$_5$ | —CH$_3$ | —CH$_3$ | O | $n_D^{23}$ = 1.4780 |
| 13 | —C$_3$H$_7$(i) | —CH$_3$ | —CH$_3$ | —CH$_3$ | O | $n_D^{23}$ = 1.4872 |
| 14 | —C$_3$H$_7$(i) | —CH$_3$ | —CH$_3$ | —CH$_3$ | S | Fp. 68–70° C. |
| 15 | —C$_3$H$_7$(i) | —C$_2$H$_5$ | —CH$_3$ | —CH$_3$ | S | $n_D^{23}$ = 1.5231 |
| 16 | —C$_4$H$_9$(n) | —CH$_3$ | —CH$_3$ | —CH$_3$ | O | $n_D^{23}$ = 1.4782 |
| 17 | —C$_4$H$_9$(n) | —CH$_3$ | —CH$_3$ | —CH$_3$ | S | $n_D^{23}$ = 1.5362 |
| 18 | —C$_4$H$_9$(n) | —C$_2$H$_5$ | —CH$_3$ | —CH$_3$ | O | $n_D^{23}$ = 1.4796 |
| 19 | —CH(CH$_3$)CH$_2$CH$_3$ | —CH$_3$ | —CH$_3$ | —CH$_3$ | O | $n_D^{23}$ = 1.4897 |
| 20 | —CH(CH$_3$)CH$_2$CH$_3$ | —CH$_3$ | —CH$_3$ | —CH$_3$ | S | Fp. 59–61° C. |
| 21 | —C$_4$H$_9$(i) | —CH$_3$ | —CH$_3$ | —CH$_3$ | O | $n_D^{23}$ = 1.4851 |
| 22 | —C$_4$H$_9$(i) | —CH$_3$ | —CH$_3$ | —CH$_3$ | S | Fp. 49–51° C. |

-continued

| Example No. | R | R₁ | R₂ | R₃ | X | Physical Data |
|---|---|---|---|---|---|---|
| 23 | —C₅H₁₁(n) | —CH₃ | —CH₃ | —CH₃ | O | $n_D^{23} = 1.4726$ |
| 24 | —C₅H₁₁(n) | —CH₃ | —CH₃ | —CH₃ | S | $n_D^{23} = 1.5321$ |
| 25 | 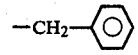 —CH₂— | —CH₃ | —CH₃ | —CH₃ | O | $n_D^{23} = 1.5344$ |
| 26 | 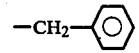 —CH₂— | —CH₃ | —CH₃ | —CH₃ | S | $n_D^{23} = 1.5758$ |
| 27 |  | —CH₃ | —CH₃ | —CH₃ | O | $n_D^{23} = 1.3617$ |
| 28 |  | —CH₃ | —CH₃ | —CH₃ | S | $n_D^{23} = 1.3562$ |
| 29 | H | —CH₃ | —CH₃ | —CH₃ | O | $n_D^{23} = 1.4538$ |
| 30 | H | —CH₃ | —CH₃ | —CH₃ | S | $n_D^{23} = 1.4725$ |
| 31 | —C₂H₅ | —CH₃ | —C₂H₅ | —C₂H₅ | O | $n_D^{20} = 1.4848$ |
| 32 | —C₄H₉(i) | —CH₃ | —C₂H₅ | —C₂H₅ | O | $n_D^{20} = 1.4771$ |
| 33 | —CH₂CH₂CN | —CH₃ | —C₂H₅ | —C₂H₅ | O | $n_D^{20} = 1.4929$ |
| 34 | —C₅H₁₁(n) | —CH₃ | —C₂H₅ | —C₂H₅ | O | $n_D^{20} = 1.4795$ |
| 35 | | | | | | |
| 36 | —C₃H₇(i) | —CH₃ | —C₃H₇(n) | —C₃H₇(n) | S | $n_D^{20} = 1.5230$ |
| 37 | —CH₂C(CH₃)₂CH₂OC₂H₅ | —CH₃ | —CH₃ | —CH₃ | O | $n_D^{25} = 1.4758$ |
| 38 | —CH₂C(CH₃)₂CH₂OC₂H₅ | —CH₃ | —CH₃ | —CH₃ | S | |
| 39 | —CH₂C(CH₃)₂CH₂OC₃H₇ | —CH₃ | —CH₃ | —CH₃ | O | |
| 40 | —CH₂C(CH₃)₂CH₂OC₃H₇ | —CH₃ | —CH₃ | —CH₃ | S | |
| 41 | —CH₂SC₂H₅ | —CH₃ | —CH₃ | —CH₃ | O | |
| 42 | —CH₂SC₂H₅ | —CH₃ | —CH₃ | —CH₃ | S | |
| 43 | 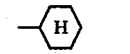 | —CH₃ | —CH₃ | —CH₃ | O | $n_D^{25} = 1.5027$ |
| 44 | 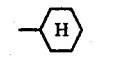 | —CH₃ | —CH₃ | —CH₃ | S | |
| 45 |  | —CH₃ | —CH₃ | —CH₃ | O | $n_D^{25} = 1.5037$ |
| 46 |  | —CH₃ | —CH₃ | —CH₃ | S | |
| 47 |  | —CH₃ | —CH₃ | —CH₃ | O | |
| 48 |  | —CH₃ | —CH₃ | —CH₃ | O | |
| 49 | 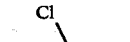 | —CH₃ | —CH₃ | —CH₃ | O | |
| 50 | 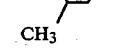 | —CH₃ | —CH₃ | —CH₃ | O | |
| 51 |  | —CH₃ | —CH₃ | —CH₃ | O | |

(B) EXAMPLES OF FORMULATION

Example a

An emulsifiable concentrate is obtained from
15 parts by weight of active substance
75 parts by weight of cyclohexanone as solvent and
10 parts by weight of oxethylated nonyl phenol (10 EO) as emulsifier.

Example b

As wettable powder which is easily dispersible in water is obtained by mixing
25 parts by weight of active substance
64 parts by weight of active silicic acid as inert material
10 parts by weight of calcium lignosulfonate and
1 part by weight of sodium oleoyl-methyl-taurine as wetting and dispersing agent and grinding the mixture in a pin mill.

Example c

A dusting powder is obtained by mixing
10 parts by weight of active substance and
90 parts by weight of talc as inert material and comminuting the mixture in a hammer mill.

Example d

A granular formulation consists, for example, of about
2 to 15 parts by weight of active substance and
98 to 85 parts by weight of inert granular material such as attapulgite, pumice and quartz sand.

(C) BIOLOGICAL EXAMPLES

Example I

Horse beans (*Vicia faba*) strongly infested with bean aphids (*Aphis craccivora*) were sprayed to the drip off with an 0.025% aqueous suspension of a wettable powder concentrate of the active compound of Example 1 and then kept in a greenhouse, 3 days after treatment it was found that all aphids had been killed. The compounds of Examples 2 to 8, 10 to 24, 29, 30, 37, 43 and 45 had the same effect. When applied in a concentration of 0.2% the compounds of Examples 9, 31 to 34 and 36 also exhibited a 100% efficiency 3 days after treatment.

Example II

Horse beans (*Vicia faba*) in pots, the root system of which had been enveloped in a plastics sheet, were infested with bean aphids (*Aphis craccivora*) and then treated each with 1 mg of active compound by uniformly distributing an aqueous dilution of an emulsion concentrate in the root system by means of a glass funnel.

Evaluation after 8 days indicated a 100% mortality with the compounds of Examples 1, 3, 5, 6, 8, 10 to 21 and 23.

What is claimed is:

1. N,N-dialkyl-O-[pyrazol-5-yl]-carbamic acid esters of the formula

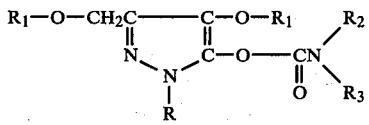

in which R is alkyl of 2 to 4 carbon atoms, unsubstituted or substituted by CN, and $R_1$, $R_2$, and $R_3$ are alkyl of 1 to 4 carbon atoms.

2. 1-Cyanoethyl-3-methoxymethyl-4-methoxy-5-dimethylcarbamoyloxy pyrazole.

3. 1-n-Propyl-3-methoxymethyl-4-methoxy-5-dimethylcarbamoyloxy pyrazole.

4. 1-n-Butyl-3-methoxymethyl-4-methoxy-5-dimethylcarbamoyloxy pyrazole.

5. An aphicidal composition comprising an aphicidally effective amount of a compound as defined in claim 1 and a carrier therefor.

6. A method for combating noxious aphids which comprises treating the aphids or the aphid infested crop plants with an effective amount of a compound as claimed in claim 1.

* * * * *